(12) United States Patent
Sarkela (10) Patent No.: US 9,579,035 B2
(45) Date of Patent: Feb. 28, 2017

(54) DETECTION OF EPILEPTIFORM ACTIVITY (75) Inventor: Mika Sarkela, Helsinki (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1837 days.

(21) Appl. No.: 11/617,151

(22) Filed: Dec. 28, 2006

(65) Prior Publication Data

US 2007/0197930 A1 Aug. 23, 2007

(30) Foreign Application Priority Data

Feb. 17, 2006 (EP) ..................................... 06110089

(51) Int. Cl.
*A61B 5/04* (2006.01)
*A61B 5/048* (2006.01)
*A61B 5/00* (2006.01)
*G06K 9/00* (2006.01)

(52) U.S. Cl.
CPC ............ *A61B 5/048* (2013.01); *A61B 5/4094* (2013.01); *A61B 5/726* (2013.01); *G06K 9/00523* (2013.01)

(58) Field of Classification Search
CPC .................................................. A61B 5/0476
USPC .................................................. 600/544, 545
See application file for complete search history.

(56) References Cited

U.S. PATENT DOCUMENTS

| 5,743,860 A | 4/1998 | Hively et al. |
| 5,857,978 A | 1/1999 | Hively et al. |
| 5,995,868 A | 11/1999 | Dorfmeister et al. |
| 6,549,804 B1 * | 4/2003 | Osorio et al. .................. 600/544 |
| 2003/0055355 A1 * | 3/2003 | Viertio-Oja ..................... 600/544 |
| 2003/0171685 A1 | 9/2003 | Lesser et al. |
| 2004/0010203 A1 * | 1/2004 | Bibian et al. .................. 600/544 |
| 2004/0068199 A1 | 4/2004 | Echauz et al. |
| 2006/0009709 A1 * | 1/2006 | Rautee et al. ................. 600/544 |
| 2006/0200038 A1 * | 9/2006 | Savit et al. .................... 600/544 |

OTHER PUBLICATIONS

Marko Znidaric, "Asymptotic Expansion for Inverse Moments of Binomial and Poisson Distributions", 2000, Mathetmatics Subject Classification. Primary 62E20 60E05.*

(Continued)

*Primary Examiner* — Christian Jang
(74) *Attorney, Agent, or Firm* — GE Global Patent Operation; Marc A. Vivenzio (57) ABSTRACT

The invention relates to detection of epileptiform activity. In order to accomplish a mechanism with improved specificity to epileptiform activity and with the capability to detect specific type of epileptic patterns, brain wave signal data obtained from a subject is decomposed into at least one predetermined subband, each subband being indicative of a specific type of epileptiform activity. The subband-specific output data obtained represents a time series of a quantitative characteristic of the brain wave signal data. At least one measure is determined for any one or more of the at least one predetermined subband, the at least one measure belonging to a measure set comprising a first measure indicative of the entropy of the subband-specific output data and a second measure indicative of a normalized form of k:th order central moment of the subband-specific output data, where k is an integer higher than three. The presence of a specific type of epileptiform activity may be detected based on the at least one measure of the respective subband.

25 Claims, 4 Drawing Sheets

(56) References Cited

OTHER PUBLICATIONS

Headrick, Todd C. Fast fifth order polynomial transforms for generating univariate and multivariate nonnormal distributions. Computational Statistics & Data Analysis 40 (2002) 685-711.*

McSharry et al.: Comparison of Predictability of Epileptic Seizures by a Linear and Nonlinear Method, IEEE Transactions on Biomedical Engineering, vol. 50, No. 5, May 2003, pp. 628-633.

T. Inouye et al.: Abnormality of background EEG determined by the entropy of power spectra in epileptic patients, Electroencephalography and clinical Neurophysiology, 82 (1992), pp. 203-207.

Rosso OA, Blanco S, Yordanova J, Kolev V, Figliola A, Schurmann M, Basar E: Wavelet entropy: a new tool for analysis of short duration brain electrical signals. Journal of Neuroscience Methods 105 (2001), pp. 65-75.

Rosso OA, Blanco S., Rabinowitz A. Wavelet analysis of generalized tonic-clonic epileptic seizures, Signal Processing 2003; 83(6): 1275-1289.

Geva AB, Kerem DH: Forecasting Generalized Epileptic Seizures from EEG Signal by Wavelet Analysis and Dynamic Unsupervised Fuzzy Clustering, IEEE Transactions on Biomedical Engineering, vol. 45, Oct. 1998, pp. 1205-1216.

Schiff et al., "Fast wavelet transformation of EEG", Electroencephalography and clinical Neurophysiology, pp. 442-445, 1994.

Kalayci et al., "Wavelet Preprocessing for Automated Neural Network Detection of EEG Spikes", IEEE Engineering in Medicine and Biology, pp. 160-166, Mar./Apr. 1995.

Figliola et al., "Analysis of Physiological Time Series Using Wavelet Transforms", IEEE Engineering in Medicine and Biology, pp. 74-79, May/Jun. 1997.

Yli-Hankala et al., "Epileptiform Electroencephalogram during Mask Induction of Anesthesia with Sevoflurane", Anesthesiology, vol. No. 91, Issue No. 6, pp. 1596-1603, Dec. 1999.

Sartoretto et al., "Automatic detection of epileptiform activity by single-level wavelet analysis", Clinical Neurophysiology vol. 110, pp. 239-249, 1999.

Paul et al., "Prediction of PTZ-Induced Seizures Using Wavelet-Based Residual Entropy of Cortical and Subcortical Field Potentials", IEEE Transactions on Biomedical Engineering,vol. No. 50, Issue No. 5, pp. 640-648, May 2003.

Khan et al., "Wavelet based automatic seizure detection in intracerebral electroencephalogram", Clinical Neurophysiology vol. 114, pp. 898-908, 2003.

Hornero et al., "Use of Wavelet Entropy to Compare the EEG Background Activity of Epileptic Patients and Control Subjects", pp. 5-8, 2003.

Huang et al., "Prediction of Epileptic Seizures Using Bispectrum Analysis of Electroencephalograms and Artificial Neural Network", pp. 2947-2949, 2003.

Al-Nashash et al., "Monitoring of Global Cerebral Ischemia Using Wavelet Entropy Rate of Change", IEEE Transactions on Biomedical Engineering, vol. No. 52, Issue No. 12, pp. 2119-2122, Dec. 2005.

\* cited by examiner

DETECTION OF EPILEPTIFORM ACTIVITY

FIELD OF THE INVENTION

The present invention relates generally to the detection of epileptiform activity. More particularly, the present invention relates to a mechanism for automatic detection of epileptiform activity in subject's brain wave data. Epileptiform activity here refers to signal waveforms or patterns which are typical in epilepsy and which may also be associated with an increased risk of seizures.

BACKGROUND OF THE INVENTION

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

The EEG signal represents the sum of excitatory and inhibitory potentials of large numbers of cortical pyramidal neurons, which are organized in columns. Each EEG electrode senses the average activity of several thousands of cortical pyramidal neurons.

The EEG signal is often divided into four different frequency bands: Delta (0.5-3.5 Hz), Theta (3.5-7.0 Hz), Alpha (7.0-13.0 Hz), and Beta (13.0-32.0 Hz). In an adult, Alpha waves are found during periods of wakefulness, and they may disappear entirely during sleep. Beta waves are recorded during periods of intense activation of the central nervous system. The lower frequency Theta and Delta waves reflect drowsiness and periods of deep sleep.

Different derangements of internal system homeostasis disturb the environment in which the brain operates, and therefore the function of the brain and the resulting EEG are disturbed. The EEG signal is a very sensitive measure of these neuronal derangements, which might be reflected in the EEG signal either as changes in membrane potentials or as changes in synaptic transmission. A change in synaptic transmission occurs whenever there is an imbalance between consumption and supply of energy in the brain. This means that the EEG signal serves as an early warning of a developing injury in the brain.

According to the present state of knowledge, the EEG signal is regarded as an effective tool for monitoring changes in the cerebral state of a patient. Diagnostically, the EEG is not specific, since many systemic disorders of the brain produce similar EEG manifestations. In Intensive Care Units, an EEG signal may be of critical value, as it may differentiate between broad categories of psychogenic, epileptic, metabolic-toxic, encephalopatic and focal conditions.

Epilepsy is the most common neurological disorder, affecting about one percent of the population at some time in their life. One proposed mechanism for the onset of an epileptic seizure is that neurons in a particular region of the brain become synchronized, leading to a reduction of EEG signal complexity in that area. The theory is proved correct by intracranial EEG recordings, cf. McSharry et al.: *Comparison of Predictability of Epileptic Seizures by a Linear and Nonlinear Method*, IEEE Transactions on Biomedical Engineering, vol. 50, No. 5, May 2003, pp. 628-633. However, when brain activity is recorded from the scalp, the measured signal is a composition originating from multiple sources and methods indicative of the complexity of the signal show an increase during a seizure, cf. U.S. Pat. Nos. 5,743,860 and 5,857,978.

Just as there are numerous seizure types, any type of seizure may manifest as status epilepticus (SE). SE is usually defined as more than 30 minutes of (1) continuous seizure activity, or (2) two or more sequential seizures without full recovery of consciousness between the seizures. Status epilepticus is often divided into convulsive and nonconvulsive types. The EEG, which demonstrates ongoing ictal activity, can be used to further subdivide SE into either generalized (abnormal activity in the whole brain) or partial SE (abnormal activity in a particular region of the brain). Convulsive status epilepticus (CSE) is the most serious, frequent, and most easily recognized type of SE. It may occur either in primary generalized epilepsy or be secondarily generalized. It is characterized by loss of consciousness and recurrent or continuous convulsions. CSE is a medical emergency and is associated with high morbidity and mortality. Nonconvulsive status epilepticus is often defined as an epileptic state of more than 30 minutes with some clinically evident change in mental status or behaviour from baseline and ictal activity in the EEG.

In status epilepticus, the epileptiform spikes typically last only for a fraction of seconds, but the use of the EEG leans towards the fact that by using long lasting recordings, the EEG signal can reflect slow trend changes. Also, if a seizure occurs during measurements, the EEG signal helps to categorize the epileptiform patterns and seizure activity as a specific type of epilepsy, as well as identify the nonconvulsive forms of status epilepticus. In addition, the EEG signal may be used as a control tool for inducing a barbiturate sleep to a level where there are no visible seizures.

Encephalopathy commonly refers to central nervous system dysfunction of any cause, and it can be classified further as either an epileptic encephalopathy or epileptiform encephalopathy. While epileptic encephalopathies are characterized by frequent seizures, epileptiform encephalopathies refer to disorders with epileptiform activity without marked clinical seizure activity. As mentioned above, epileptiform activity commonly refers to signal waveforms or patterns which are typical in epilepsy and which may also be associated with an increased risk of seizures. However, due to the relationship between epilepsy and encephalopathy, similar waveforms or patterns may also appear in other states than in epilepsy, such as in encephalopathy. It is also to be noted in this context that detected epileptiform activity does not alone confirm a diagnosis, but the patient needs to be further examined.

Most of the metabolic and systemic disorders have EEG correlates, and if there is a disturbance of conscious level, the EEG is never normal. However, the EEG findings in encephalopathy have many similarities to those during sedation and anesthesia, which makes the detection of encephalopathy in sedated patients difficult. Generally, when a patient loses consciousness, a shift of spectral power towards lower frequencies appears. Generalized slowing apply also in the case of encephalopathy, however additive periodical and miscellaneous patters often appear in the EEG. Periodical patterns can be, for example, periodic lateralizing epileptiform discharge (PLED) or burst suppression. Miscellaneous patterns are, for example, triphasic waves. Triphasic waves occur about 20-25% of the hepatic encephalopathy patients being, however, not a specific feature for this disease only. They can occur also in other metabolic diseases and noncolvusive status epilepticus.

In epilepsy, the EEG may include spiky waveforms. While the frequency contents of the spikes may reach up to about 70 Hz, the epileptiform EEG activity is typically below 30 Hz. Periodical patterns of lower frequencies are also typical to epileptiform activity. These patterns include, for example, periodic epileptiform discharges and spike-wave-complexes.

Numerous automatic techniques have been described for the detection and prediction of epileptiform activity. Most of the known methods utilize the whole spectra of an EEG signal. Therefore, the methods are not enough specific to the epileptiform activity only. For example, a spectral entropy has been utilized for investigating the relationships between epileptiform discharges and background EEG activity, cf. T. Inouye et al.: *Abnormality of background EEG determined by the entropy of power spectra in epileptic patients*, Electroencephalography and clinical Neurophysiology, 82 (1992), pp. 203-207. Epileptiform activity increases the spectral entropy values of the EEG signal data, but the values still remain below the baseline of a conscious patient. The above-mentioned U.S. Pat. Nos. 5,743,860 and 5,857,978 in turn describe analysis methods in which the detection of epileptic seizures is based on non-linear measures of the signal data, such as Kolmogorov entropy. The signal data may be EEG signal data or magnetoencephalographic (MEG) signal data. MEG is indicative of the magnetic component of brain activity, i.e. it is the magnetic counterpart of EEG.

Methods based on wavelet transformation of the EEG signal data have also been proposed for analyzing brain signals, cf. Rosso O A, Blanco S, Yordanova J, Kolev V, Figliola A, Schurmann M, Basar E: *Wavelet entropy: a new tool for analysis of short duration brain electrical signals*. Journal of Neuroscience Methods 105 (2001), pp. 65-75. In this method, entropy is calculated from the power distribution between the decomposition levels of the transform. In that sense, the technique is thus related to the determination of spectral entropy. However, spectral information is now derived by means of a wavelet transform instead of a Fourier transform.

The article Rosso O A, Blanco S., Rabinowitz A. *Wavelet analysis of generalized tonic-clonic epileptic seizures*, Signal Processing 2003; 83(6): 1275-1289, describes a wavelet-based method for the analysis of generalized tonic-clonic epileptic seizures. The identification of these seizures is aggravated by the simultaneous muscle activity disturbing the EEG signal. The article describes that wavelet entropy corresponding to a frequency band of 0.8 to 12.8 Hz is lower during seizures than during pre- and post-seizure periods. When a wider frequency band of 0.8 to 51.2 Hz is used, the wavelet entropy first increases at the beginning of seizure, which might be caused by muscle activity.

A further wavelet-based method for analyzing an EEG is described in Geva A B, Kerem D H: *Forecasting Generalized Epileptic Seizures from EEG Signal by Wavelet Analysis and Dynamic Unsupervised Fuzzy Clustering*, IEEE Transactions on Biomedical Engineering, vol. 45, October 1998, pp. 1205-1216. The method, which is intended for forecasting a generalized epileptic seizure, relies on the existence in the EEG of a preseizure state and utilizes fuzzy clustering for classifying temporal EEG patterns.

One drawback related to the above techniques for automatic detection of epileptiform activity is the weak specificity to epileptiform activity. Therefore, epileptiform activity cannot be distinguished from changes in the level of consciousness of the patient. For example, in the above-described methods based on wavelet entropy the entropy values obtained during an epileptic seizure are typically between the wavelet entropies of the conscious and unconscious states of a patient. Therefore, the methods cannot distinguish, for example, whether an increase in the wavelet entropy is caused by an epileptiform EEG of anesthetized patient or the arousal of the patient.

A further drawback of the prior art detection techniques is that they cannot indicate when a specific type of epileptiform activity is present in the EEG or which type of epileptiform waveforms are present in the EEG signal. Many of the algorithms are also rather complex and require high computation power, which makes them unsuitable for ambulatory devices.

The present invention seeks to eliminate the above-mentioned drawbacks and to bring about a mechanism for detecting epileptiform activity with improved specificity and with the capability to detect specific type of epileptiform signal patterns in the brain wave data obtained from a patient.

SUMMARY OF THE INVENTION

The present invention seeks to provide a novel mechanism that enables automatic and reliable detection of epileptiform activity in brain wave signal data, regardless of possible changes in patient's level of consciousness. The present invention further seeks to provide a mechanism which enables detection of specific epileptiform waveforms and which is efficient in terms of the computation power required.

In the present invention, brain wave signal data obtained from a subject is decomposed to obtain subband-specific output data for at least one subband of the original brain wave signal data, each subband corresponding to a specific type of epileptiform waveforms. The output data represents a time series of a quantitative characteristic, such as signal amplitude, of the brain wave signal data on the subband in question. The said data is typically obtained by a filtering process which may also yield, in certain embodiments of the invention, wavelet coefficients as the quantitative characteristic. The filtering process is carried out by at least one filter, though typically by a filter bank, and it provides the said output data for each subband of interest. In outputting the said time series, the filtering process of the invention differs from an ordinary spectral analysis, where the output dimensions are typically signal frequency and signal power. The filtering process of the invention may be carried out by finite impulse response (FIR) or infinite impulse response (IIR) filters, or by a wavelet-based filter bank, for example. The waveforms of interest are detected by calculating the entropy and/or kurtosis of the time-domain output data of the subband concerned. The decision on the presence of specific epileptiform waveforms may then be made based on the entropy and/or kurtosis values obtained for the subband related to the said waveforms. The decision may be made automatically by the apparatus of the invention, or the apparatus of the invention may simply display the subband-specific entropy and/or kurtosis values, which indicate whether or not specific epileptiform waveforms are present. The values may or may not be accompanied by additional information assisting the user of the apparatus to make a final decision on the presence/absence of epileptiform waveforms of a specific type.

Subband-specific entropy and kurtosis are both good indicators of epileptiform activity and may be used either alone or in combination to indicate epileptiform activity on the respective subband. However, as discussed below, kurtosis, which is a normalized form of the fourth central moment, may also be replaced by a normalized form of a central moment of an order higher than four. The brain wave signal data to which the wavelet transform is applied is typically EEG signal data, but may also be obtained through a standard MEG recording.

A wavelet transform offers an efficient way to implement the decomposition process, because 1) it may be used simultaneously for data compression, 2) it typically provides orthogonal outputs between adjacent frequency bands, 3) its sensitivity to epileptiform patterns may be tuned with a proper mother wavelet selection, and 4) it is computationally efficient, since filters with narrow frequency bands may be implemented with a relatively low order of filter coefficients. In case of wavelet-based filtering, the wavelet coefficients thus represent the quantitative characteristic whose time series is output for each subband of interest. In a FIR or IIR based filtering, the quantitative characteristic may be signal amplitude or power, for example.

Thus one aspect of the invention is providing a method for detecting epileptiform activity. The method includes obtaining brain wave signal data from a subject and decomposing the brain wave signal data into at least one predetermined subband, to obtain subband-specific output data representing a time series of a quantitative characteristic of the brain wave signal data, wherein each subband is indicative of a specific type of epileptiform activity. The method further includes (i) determining at least one measure for at least one of the at least one predetermined subband, the at least one measure belonging to a measure set comprising a first measure indicative of the entropy of the subband-specific output data and a second measure indicative of a normalized form of k:th order central moment of the subband-specific output data, where k is an integer higher than three and (ii) indicating, based on the at least one measure of the respective subband, whether a specific type of epileptiform activity is present in the brain wave signal data.

As the original brain wave signal data is decomposed into one or more subbands on which epileptiform waveforms of interest appear, the detection mechanism of the invention rests efficiently on the morphology of the brain wave signal.

Another aspect of the invention is that of providing an apparatus for detecting epileptiform activity. The apparatus includes measurement means for obtaining brain wave signal data from a subject and signal processing means for decomposing the brain wave signal data into at least one predetermined subband, each subband being indicative of a specific type of epileptiform activity and the signal processing means being configured to provide subband-specific output data representing a time series of a quantitative characteristic of the brain wave signal data. The apparatus further includes (i) calculation means for determining at least one measure for at least one of the at least one predetermined subband, the at least one measure belonging to a measure set comprising a first measure indicative of the entropy of the subband-specific output data and a second measure indicative of a normalized form of k:th order central moment of the subband-specific output data, where k is an integer higher than three and (ii) indicator means for indicating, based on the at least one measure of the respective subband, whether a specific type of epileptiform activity is present in the brain wave signal data.

The entropy and/or kurtosis values obtained during a seizure are clearly different from the values caused by changes in the level of consciousness, which makes the mechanism suitable for monitoring epileptiform activity in connection with anesthesia or in any other environment where the level of consciousness of the patient may vary.

Since the detection may be made by a direct comparison between the subband-specific measurement value, such as entropy, and a predetermined threshold value, the mechanism does not require high computation power. Therefore, the mechanism of the invention may find use outside clinical environment in devices with limited computation power.

In a still further embodiment, the invention provides a computer program comprising computer program code means adapted to perform the above decomposing, determining, and detecting steps of the method when run on a computer. It is thus to be noted that since a conventional EEG/MEG measurement device may be upgraded by a plug-in unit that includes software enabling the measurement device to detect certain epileptiform waveforms, the plug-in unit does not necessarily have to take part in the acquisition of the brain wave signal data.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 8 in the appended drawings, wherein.

DETAILED DESCRIPTION OF THE INVENTION

Below, different embodiments of the invention are discussed assuming that the brain wave signal data measured from the patient is EEG signal data and that either one or both of the entropy and kurtosis of the subband-specific output data is/are used as the indicator(s) of epileptiform activity.

Figure 1:
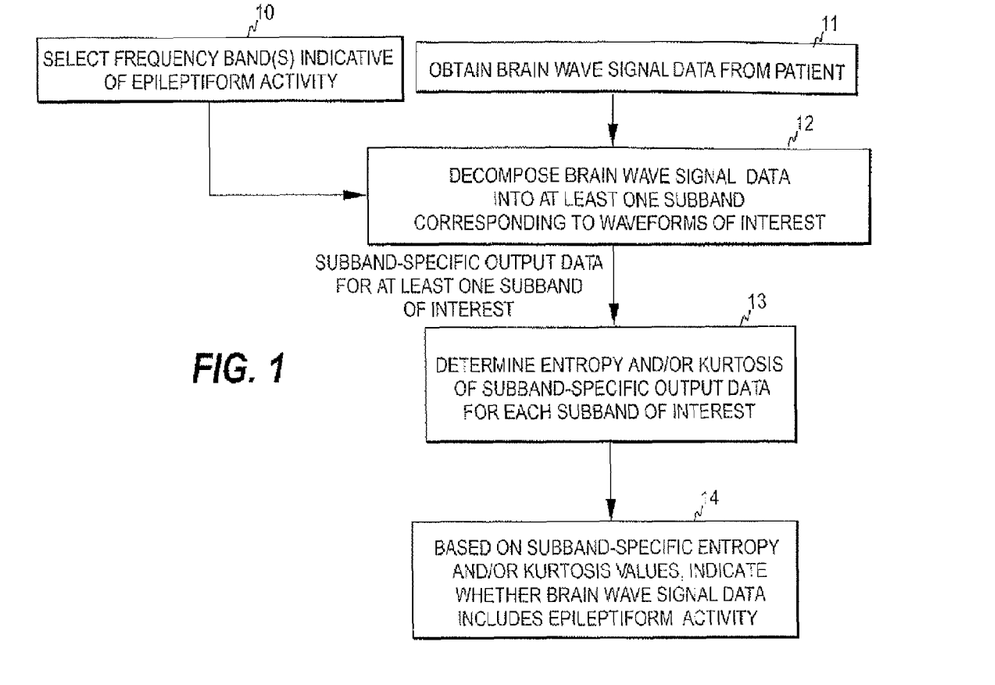
FIG. 1 illustrates one embodiment of the method of the invention.

FIG. 1 is a flow diagram illustrating the detection mechanism of the invention. As discussed above, the epileptiform EEG activity may include spiky waveforms. Although the frequency contents of the spikes may reach up to about 70 Hz, epileptiform EEG components are typically below 30 Hz. In the present invention, at least one EEG frequency band is selected, which contains epileptiform activity (step 10) and the raw EEG signal data obtained from a patient is decomposed into at least one subband on which the waveforms of interest appear (steps 11 and 12) so as to obtain subband-specific output data for each of the at least one subband. For example, if epileptiform spikes are to be detected, the wavelet transform may be employed to decompose the EEG signal data into one or more subbands on which epileptiform spikes appear. The subband-specific output data represents a time series of a quantitative characteristic of the brain wave signal data on the subband in question. The quantitative characteristic may be signal amplitude or signal power, for example, and also a wavelet coefficient. The decomposition may be performed by any suitable signal processing method. However, the decomposition typically involves a filtering process.

As a result of the decomposition, at least one time series of a quantitative characteristic is obtained, i.e. one time series for each subband of interest. For each subband of interest, the entropy and/or kurtosis of the quantitative characteristic is/are determined (step 13). Based on the subband-specific entropy and/or kurtosis value(s), the system then indicates whether epileptiform activity is present in the EEG signal (step 14).

In one embodiment of the invention, the presence/absence of epileptiform activity is indicated by displaying the entropy and/or kurtosis values obtained for each subband of interest. Based on the subband-specific values, the user of the system then knows whether waveforms of a specific type are present in the EEG signal. In another embodiment of the invention, the detection is automatic so that the apparatus makes the decision on the presence/absence of waveforms of a specific type and presents the results to the user. As discussed below, the automatic detection may involve a comparison of the subband entropy/kurtosis values with a predetermined threshold.

Figure 2:
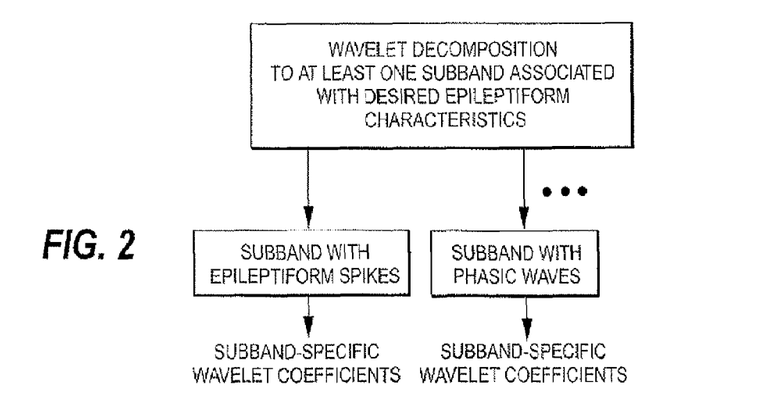
FIG. 2 illustrates the use of a wavelet transform for detecting epileptiform waveforms.

FIG. 2 illustrates the use of the wavelet transform for detecting certain epileptiform waveforms. As discussed above, a wavelet-based filter bank, i.e. a filter bank configured to perform a wavelet transform, may be employed to decompose the EEG signal into subbands so that at least one of the subbands corresponds to the waveforms of interest. For example, the wavelet transform may decompose the signal to two subbands on which epileptiform spikes occur, such as 16 to 32 Hz and 32 to 64 Hz, and to two further subbands on which phasic waves (triphasic, diphasic or monophasic) occur, such as 2 to 4 Hz and 4 to 8 Hz. The entropy and/or kurtosis of the wavelet coefficients of the desired subbands are then calculated to determine whether the respective waveforms are present in the EEG signal.

Figures 3, 4:
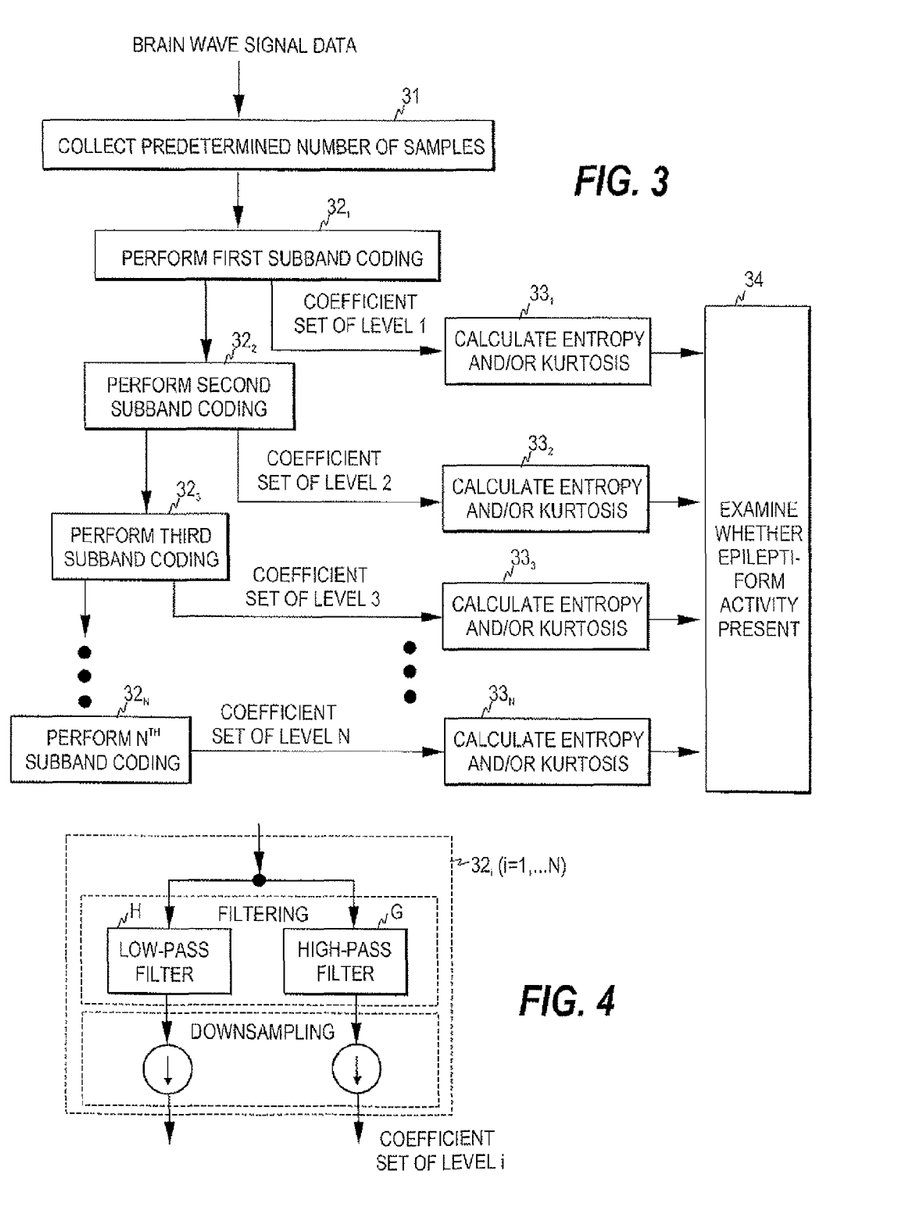
FIG. 3 illustrates an embodiment of the invention employing discrete wavelet transform.
FIG. 4 illustrates the subband coding in the embodiment of FIG. 2.

FIG. 3 illustrates an embodiment in which discrete wavelet transform is employed to decompose the EEG signal. The incoming EEG signal is sampled at a predetermined sampling frequency and therefore the process first collects a predetermined number of samples representing the signal in a time window of a predetermined length (step 31). As is common in the art, the digitized signal samples are processed as sets of sequential signal samples representing finite time blocks or time windows, commonly termed "epochs". Each epoch is supplied to a subband coding process which may be performed N(N=1, 2, . . . ) times (steps $32_1$ to $32_N$). Subband coding here refers to the filtering and downsampling operations performed at each decomposition level of a discrete wavelet transform. FIG. 4 illustrates the said operations. As common in discrete wavelet transforms, at each decomposition level the original signal is first passed through a high-pass filter G and a low-pass filter H. After the filtering, part of the samples, typically half, is discarded in a downsampling process. The output of the high-pass filter constitutes the wavelet coefficients of the respective decomposition level.

With reference back to FIG. 3, the subband coding is thus performed N times, each subband coding corresponding to a certain decomposition level. The value of N depends on the waveforms of interest (and sample frequency); the subband coding is repeated until each subband of interest is available. At each decomposition level, a set of wavelet coefficients is obtained for each epoch of EEG samples. As discussed below, the number of coefficients in a set may depend on various parameters, such as the decomposition level. Set-specific entropy and/or kurtosis values are then calculated. The calculation is performed for at least the sets corresponding to the desired subbands, although the said values may be calculated for all sets (steps $33_1$ to $33_N$).

The wavelet coefficients are either positive or negative real numbers. For the purposes of entropy calculation, it is advantageous to multiply the coefficients to the power of two and normalize their sum equal to one.

Normalization makes the detection mechanism insensitive to interindividual differences in EEG amplitudes. After the normalization of the coefficients, the entropy H of a coefficient set may be calculated for each subband according to the following formula:

$$H = -\sum_i c_i \log c_i,$$

where $c_i$ represents the normalized coefficients in the set. Entropy values may further be normalized between 0 and 1 by dividing them by the logarithm of the number of coefficients in the set. Since each subband coding reduces the number of coefficients obtained, normalization facilitates the comparison of the entropy values between the subbands. The entropy H obtained is indicative of the level of peakedness or flatness in the coefficient set. The entropy formula described above corresponds to so-called Shannon entropy, which represents one possibility for calculating the entropy of the system. Other entropies, like Rényi entropy, Tsallis entropy, Kolmogorov complexity, or any other formula representing the disorder of the wavelet coefficients may also be employed.

The central moment $m_k$ of order k of a distribution is defined as:

$$m_k = E(x-\mu)^k,$$

where $\mu$ is the mean of sample set x, and E represents expected value. The normalized form of the k:th order central moment, where k is greater than two, can be calculated by dividing the k:th order central moment by the second order central moment raised to the power of k/2. The second order central moment is commonly known as the variance, whereas the normalized forms of the third and fourth order central moments are called skewness and kurtosis, respectively.

Kurtosis indicates how outlier-prone a distribution is. The kurtosis of the normal distribution is 3. Distributions that are more outlier-prone than the normal distribution have kurtosis values greater than 3, while distributions that are less outlier-prone have kurtosis values smaller than 3. The kurtosis of wavelet coefficients d in a set is defined as follows:

$$\text{kurtosis} = \frac{E(d-\mu)^4}{\sigma^4}$$

where $\mu$ is the mean of the wavelet coefficients d in the set and $\sigma$ is the standard deviation of the coefficients d. Similarly as with entropy, multiplication of coefficients to the power of two and normalization with the number of coefficients in the set is optional in connection with kurtosis calculation.

Although kurtosis, i.e. the normalized form of the fourth central moment, is used in this context as a subband-specific indicator of epileptiform activity, it is to be noted that normalized forms of higher central moments, such as the fifth or sixth order central moment, may also be used, alone or together with entropy, as subband-specific indicators of epileptiform activity.

In case of automatic detection of the epileptiform waveforms, the subband-specific entropy and/or kurtosis values may then be supplied to a decision-making unit, which decides whether epileptiform activity is present in the EEG signal. In the decision-making unit, the decision on the presence of the epileptiform waveforms may be made by comparing the entropy and/or kurtosis value of the respective subband to a corresponding threshold value. Since subband entropy decreases during epileptiform activity, the decision-making unit may decide that certain waveforms are present in the EEG signal if the entropy of any of the respective subband drops below the corresponding threshold. As discussed below, kurtosis behaves in an opposite manner, i.e. increases during epileptiform activity. Therefore, if kurtosis is used as the sole indicator, the decision-making unit may decide that epileptiform waveforms are present in the EEG signal if the kurtosis of the respective subband exceeds the corresponding threshold. Entropy and kurtosis may also be used mixed so that for one or more of the coefficient sets entropy is calculated, while kurtosis is calculated for the other coefficient sets obtained. Both the entropy and kurtosis of a coefficient set may also be calculated, although this increases the computational load.

Since the frequency band on which epileptiform activity occurs extends approximately from 2 Hz to 70 Hz, the sampling frequency may be, for example, 128 Hz. The coefficients of the first decomposition level then correspond to a subband of 32 to 64 Hz (if dyadic sampling is used), the coefficients of the second level to a subband of 16 to 32 Hz, the coefficients of the third level to a subband of 8 to 16 Hz, the coefficients of the fourth level to a subband of 4 to 8 Hz, and the coefficients of the fifth level to a subband of 2 to 4 Hz. By performing five successive subband coding processes the frequency band on which epileptiform activity may occur may thus be divided into five successive subbands. The coefficient sets corresponding to the waveforms of interest may then be supplied to further processing. For example, epileptiform spikes could be detected based on sets of the first and/or second decomposition level(s), while phasic waves and periodic epileptiform patterns may be detected based the sets of the fourth and/or fifth decomposition level(s). If a downsampling wavelet transform is employed, one new wavelet coefficient is obtained at the first decomposition level after two new EEG samples and at the second decomposition level after four new EEG samples, etc. If the length of the epoch is 5 seconds, for example, one epoch then corresponds to 320 wavelet coefficients at the first decomposition level and 160 wavelet coefficients at the first decomposition level, etc. The entropy/kurtosis values may be updated for each epoch, although the update may also be performed more frequently, such as once in a second if a 5-sec epoch is employed. The 5-sec epoch is suitable for anesthetic applications, while in ICU applications the length of the epoch is typically longer than that, of the order of 30 seconds.

Figure 5A:
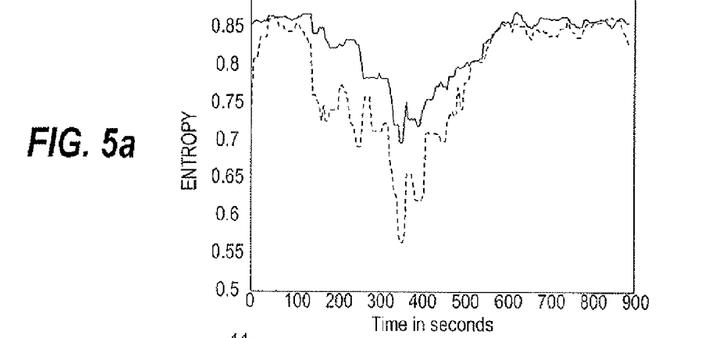
FIGS. 5a and 5b illustrate, respectively, examples of the entropy and kurtosis values obtained before, during and after an epileptiform EEG activity.
Figure 5B:
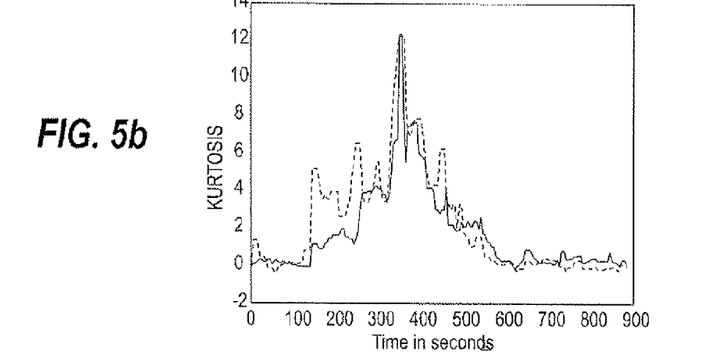

The mother wavelet to be used for the wavelet transform belongs preferably to the Daubechies (db) family or to the Symmlet (symm) family, since these families include wavelets that have a good match for actual epileptiform waveforms. Furthermore, it is advantageous to employ a basis function of a relatively low order, such as two or three, since the low order basis functions of a family represent epileptiform patterns better than the high order basis functions of the same family. This is because the basis functions become smoother and more oscillatory, i.e. less spiky, when the order increases. The specificity of the basis functions to spiky waveforms thus declines as the order increases. FIGS. 5a and 5b illustrates the subband entropy and kurtosis, respectively, during a surgery when Daubechies wavelet of order 2 is used as the mother wavelet in the transform. The continuous lines represent the entropy and kurtosis obtained from the first decomposition level, while the dashed lines represent the entropy and kurtosis obtained from the second decomposition level. The patient has fallen asleep around time 100 and epileptiform activity occurs about between time instants 150 and 600. As can be seen from the figures, entropy and kurtosis behave roughly in opposite manners; entropy decreases and kurtosis increases during epileptiform activity.

Figure 6A:
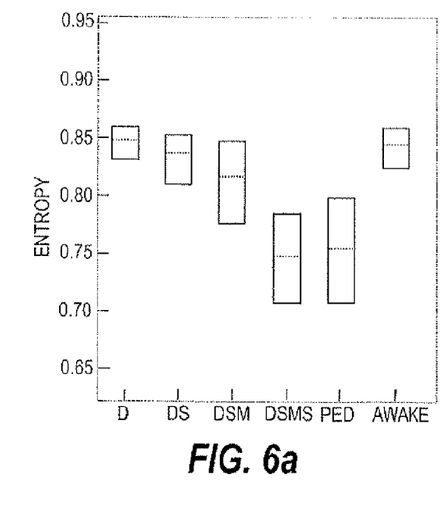
FIGS. 6a to 6d illustrate the ability of the present invention to separate different epileptiform patterns.
Figure 6B:
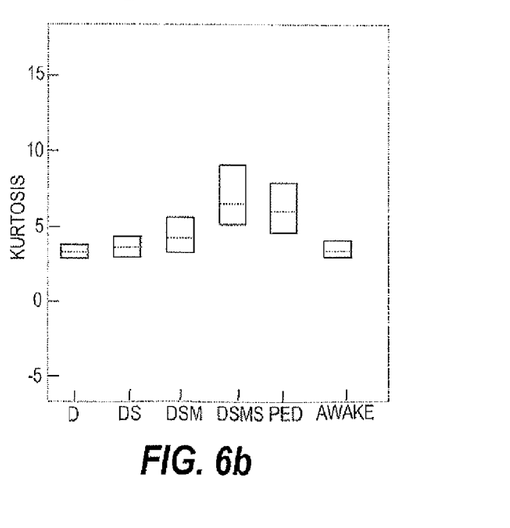
Figure 6C:
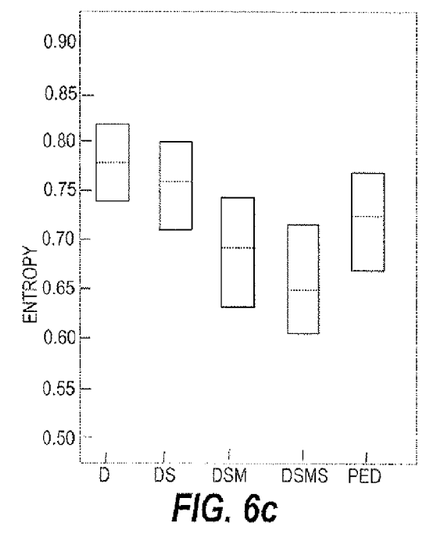
Figure 6D:
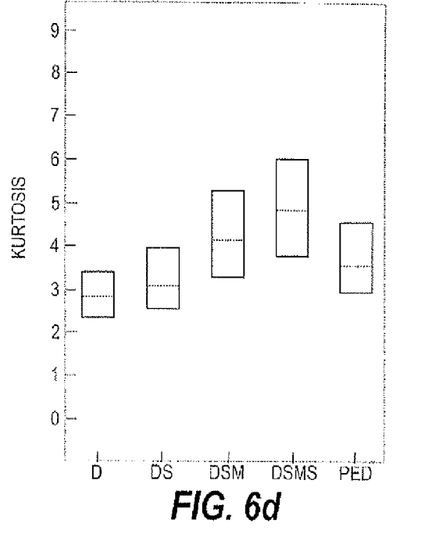

FIGS. 6a to 6d further illustrate the capability of the present invention to separate different epileptiform patterns. FIGS. 6a and 6b illustrate, respectively, the entropy and kurtosis values of the coefficients of the above-mentioned second decomposition level, while FIGS. 6c and 6d illustrate, respectively, the entropy and kurtosis values of the coefficients of the above-mentioned fifth decomposition level. In each of the figures, the vertical axis shows the entropy or kurtosis values, while horizontal axis represents different EEG patterns. The abbreviations of the different EEG patterns are as follows:

D delta
DS delta slow,
DSM delta slow monophasic,
DSMS delta slow monophasic with spikes,
PED periodic epileptiform discharges, and
AWAKE typical EEG pattern when the subject is awake.

The horizontal dashed line within each box illustrated represents a median value measured from 60 subjects, while the edges of the box correspond to the 25% and 75% quartiles. As can be seen from FIGS. 6a and 6b, the kurtosis and/or entropy values of the coefficients of the second decomposition level allow the spiky waveforms (DSMS+PED) to be separated from the non-spiky waveforms (DSM). The entropy and/or kurtosis values corresponding to the fifth decomposition level in turn allow slowed epileptiform brain waves (DSM+DSMS) to be separated from normal slowed brain waves (D+DS).

If the subband-specific output data comprises a time series of signal amplitude or signal power, the entropy and kurtosis calculated still behave in the above-described manner. Therefore, the automatic detection may in these embodiments be performed similarly as above, i.e. by comparing the entropy and/or kurtosis values with the respective threshold(s).

Figure 7:
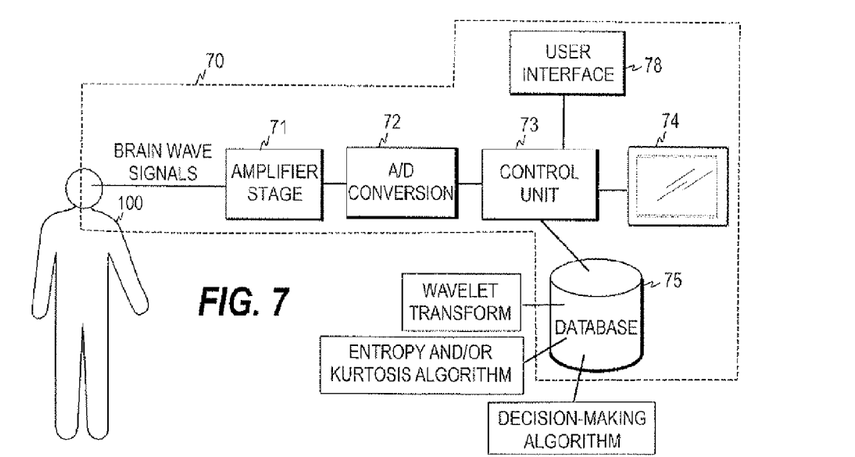
FIG. 7 illustrates one embodiment of the apparatus according to the invention.

FIG. 7 illustrates one embodiment of the system according to the invention. As mentioned above, the brain wave data acquired from a patient is typically EEG signal data. The EEG signal is typically measured from the forehead of the patient, which is a preferred measurement site due to the ease of use of the measurement and the reduced inconvenience caused to the patient.

The signals obtained from the EEG sensors are supplied to an amplifier stage, which amplifies the signals before they are sampled and converted into digitized format in an A/D converter. The digitized signals are then supplied to a control unit (including a microprocessor), which may then record the signals as an EEG time series.

The control unit is provided with a database or memory unit holding the digitized EEG signal data obtained from the sensors. Before the actual detection algorithm, the control unit may perform various pre-processing phases for improving the quality of the EEG signal data. The actual recording of the EEG signal data thus occurs in a conventional manner, i.e. the measurement device including the above elements serves as a conventional EEG measurement device. However, certain parameters, such the sampling frequency of the device, may be set according to the requirements of the decomposition process so that the separated frequency bands correspond to the epileptiform waveforms of interest.

Figure 8:
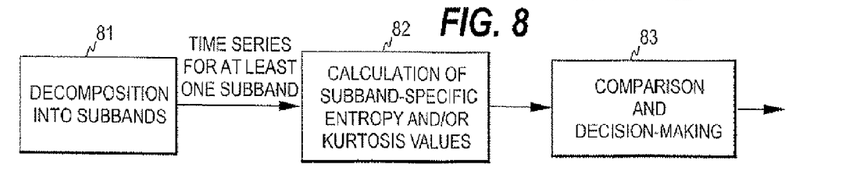
FIG. 8 illustrates the operational units of the control unit of FIG. 7 for detecting epileptiform activity in the EEG signal data.

Additionally, the control unit is provided with the above-described algorithms for detecting epileptiform waveforms in the EEG signal data. As shown in FIG. 8, the control unit may thus include three successive operational entities: a first entity for decomposing the EEG signal data in order to obtain the output data (time series) for the desired subbands, a second entity for calculating the subband-specific entropy and/or kurtosis values based on the time series, and a third entity for comparing the subband-specific values with corresponding thresholds and for making a decision on the presence of the respective waveforms in the EEG signal data. The subband-specific presence information obtained is typically Boolean type information (true/false).

As discussed above, the first entity typically includes a wavelet-based filter bank yielding a time series of wavelet coefficients, but may also include at least one filter yielding a time series of signal amplitude or signal power for the desired subband(s). In a simplified embodiment of the invention, the third entity may also be an indicator module that presents the subband-specific entropy and/or kurtosis values to the user so that the user may deduce whether epileptiform waveforms of a specific type are present.

Although one control unit (processor) may perform the calculations needed, the processing of the EEG signal data obtained may also be distributed among different processors (servers) within a network, such as a hospital LAN (local area network). For example, a conventional measurement device may record the EEG signal data and an external processor may be responsible for detecting the epileptiform waveforms in the said data.

The control unit may display the results on the screen of a monitor connected to the control unit. This may be carried out in many ways using textual and/or graphical information about the presence of certain waveforms or patterns. The information displayed may also comprise the subband-specific entropy and/or kurtosis values, with or without the associated threshold values.

The system further includes user interface means through which the user may control the operation of the system.

As discussed above, the brain wave data may also be acquired through a standard MEG recording. The measurement device may thus also serve as a conventional MEG measurement device, although a MEG measuring arrangement is far more expensive than an EEG measuring arrangement. The software enabling a conventional EEG or MEG measurement device to detect epileptiform waveforms may also be delivered separately to the measurement device, for example on a data carrier, such as a CD or a memory card, or through a telecommunications network. In other words, a conventional EEG or MEG measurement device may be upgraded by a plug-in unit that includes software enabling the measurement device to detect certain epileptiform waveforms based on the signal data it has obtained from the patient.

Since the algorithm for detecting the waveforms does not require high computation power, it may be used in various ambulatory devices, such as portable patient monitors, for monitoring epileptiform waveforms. The algorithm may also be introduced into various devices operating outside a clinical environment, such as mobile phones, PDA devices, or vehicle computers, which allows the monitoring of possible epileptic symptoms during day-to-day activities.

Although the invention was described above with reference to the examples shown in the appended drawings, it is obvious that the invention is not limited to these, but may be modified by those skilled in the art without departing from the scope and spirit of the invention. For example, the number of subbands and their limits may vary according to the epileptiform waveforms of interest, and in wavelet-based embodiments continuous wavelet transform, discrete wavelet transform, or wavelet packet transform may be used.

What is claimed is:
1. A method for detecting epileptiform activity with an epileptiform activity analysis apparatus, the epileptiform activity analysis apparatus including brain wave measurement sensors, an amplifier stage, an A/D converter, a control unit and a monitor screen, the control unit including a microprocessor, memory, a subband-specific transfer means and a calculating means, the method comprising:
obtaining brain wave signal data from sensors applied to a subject, and transmitting the brain wave signal data from the brain wave measurement sensors to the amplifier stage;
amplifying the brain wave signal data using the amplifier stage to form amplified brain wave signal data;
transmitting the amplified brain wave signal data from the amplifier stage to the A/D converter;
converting the amplified brain wave signal data using the A/D converter to digitized amplified brain wave signal data;
transmitting the digitized amplified brain wave signal data from the A/D converter to the control unit;
decomposing, using the subband-specific transfer means, the digitized amplified brain wave signal data into at least one predetermined subband, wherein each subband includes at least one waveform indicative of a specific type of epileptiform activity, and to provide subband-specific time-series data for each of the at least one predetermined subband;
determining, using the calculating means, at least one measure for each of the at least one predetermined subband, the at least one measure belonging to a measure set comprising a first measure indicative of the entropy of the subband-specific time-series data of the respective subband and a second measure indicative of a normalized form of k:th order central moment of the subband-specific time-series data of the respective subband, where k is an integer higher than three;
indicating the presence of a specific type of epileptiform activity in the brain wave signal data based on the at least one measure of the respective subband regardless of the subject's level of consciousness; and displaying on the monitor screen the presence of the specific type of epileptiform activity in the brain wave signal data of the subject in order to monitor for possible epileptic symptoms.

2. A method according to claim 1, wherein the brain wave signal data is selected from a group including electroencephalogram (EEG) signal data and magnetoencephalogram (MEG) signal data.

3. A method according to claim 1, wherein the decomposing includes employing at least one filter to obtain the subband-specific time-series output data.

4. A method according to claim 3, wherein the at least one filter is configured to perform a wavelet transform.

5. A method according to claim 4, wherein the wavelet transform is a discrete wavelet transform.

6. A method according to claim 4, wherein the wavelet transform has a basis function from a group of Daubechies wavelets or from a group of Symlet wavelets.

7. A method according to claim 1, wherein at least one of the at least one predetermined subband is indicative of epileptiform spikes or of phasic waveforms.

8. A method according to claim 1, wherein the determining includes determining one measure for each predetermined subband.

9. A method according to claim 1, wherein the indicating includes comparing the at least one measure of each predetermined subband with a respective threshold value, whereby a comparison result is obtained for each predetermined sub-band; and
deciding on the presence of a specific epileptiform activity in the brain wave signal data based on the comparison result of the respective subband, thereby to obtain presence information.

10. The method according to claim 1, wherein the second measure is indicative of normalized form of k:th order central moment $m_k$ of the subband-specific time-series data, where $m_k=E[(X-\mu)^K]/(E[(X-\mu)^2])^{k/2}$, where $\mu$ is a mean of a sample set x of the subbband-specific time-series data, and E represents an expected value, and k is an integer higher than four.

11. An apparatus for detecting epileptiform activity, the apparatus comprising:
measurement means for obtaining brain wave signal data from a subject;
subband-specific transform means configured to decompose the brain wave signal data into at least one predetermined subband, each subband being indicative of a specific type of epileptiform activity and to provide subband-specific time-series data for each of the at least one predetermined subband;
calculation means for determining at least one measure for each of the at least one predetermined subband, the at least one measure belonging to a measure set comprising a first measure indicative of the entropy of the subband-specific time-series data of the respective subband and a second measure indicative of a normalized form of k:th order central moment of the subband-specific time-series data of the respective subband, where k is an integer higher than three; and
indicator means for indicating the presence the specific type of epileptiform activity in the brain wave signal data of the subject in order to monitor for possible epileptic symptoms based on the at least one measure of the respective subband regardless of the subject's level of consciousness.

12. An apparatus according to claim 11, wherein the measurement means are configured to provide the brain wave signal data from a group including electroencephalogram (EEG) signal data and magnetoencephalogram (MEG) signal data.

13. An apparatus according to claim 11, wherein the subband-specific transform means comprise at least one filter.

14. An apparatus according to claim 13, wherein the at least one filter is configured to perform a wavelet transform.

15. An apparatus according to claim 14, wherein the at least one filter is configured to perform a discrete wavelet transform.

16. An apparatus according to claim 14, wherein the at least one filter is configured to perform a wavelet transform having a basis function from a group of Daubechies wavelets or from a group of Symlet wavelets.

17. An apparatus according to claim 11, wherein at least one of the at least one predetermined subband is indicative of epileptiform spikes or of phasic waveforms.

18. An apparatus according to claim 11, wherein the calculation means is configured to determine one measure for each predetermined subband.

19. An apparatus according to claim 11, wherein the indicator means is configured to
compare the at least one measure of each predetermined subband with a respective threshold value, thereby to obtain a comparison result for each predetermined sub-band;
decide on the presence of a specific epileptiform activity in the brain wave signal data based on the comparison result of the respective subband, thereby to obtain presence information; and
present the presence information to a user.

20. An apparatus according to claim 11, wherein the indicator means is configured to present the at least one measure to a user.

21. An apparatus according to claim 11, wherein the second measure is indicative of the kurtosis of the wavelet coefficients of the respective subband.

22. The apparatus according to claim 11 wherein the second measure is indicative of a normalized form of k:th order central moment $m_k$ of the subband-specific time-series data, where k is an integer higher than three, and where $m_k=E[(X-\mu)^k]/(E[(x-\mu)^2])^{k/2}$, where $\mu$ is a mean of a sample set x of the subband-specific time-series data, and E represents an expected value.

23. An apparatus for detecting epileptiform activity, the apparatus comprising:
a measurement module configured to obtain brain wave signal data from a subject;
a subband-specific transform module configured to decompose the brain wave signal data into at least one predetermined subband, each subband being indicative of a specific type of epileptiform activity and the subband-specific transform module being configured to provide subband-specific time-series data for each of the at least one predetermined subband,
a calculation module configured to determine at least one measure for each of the at least one predetermined subband, the at least one measure belonging to a measure set comprising a first measure indicative of the entropy of the subband-specific time-series data of the respective subband and a second measure indicative of a normalized form of k:th order central moment of the subband-specific time-series data of the respective subband, where k is an integer higher than three; and
an indicator module configured to indicate the presence of the specific type of epileptiform activity in the brain wave signal data of the subject in order to monitor for possible epileptic symptoms based on the at least one measure of the respective subband regardless of the subject's level of consciousness.

24. An apparatus according to claim 23, wherein the subband-specific transform module comprises at least one filter.

25. An apparatus according to claim 24, wherein the at least one filter is configured to perform a wavelet transform.

* * * * *